(12) United States Patent
Ye et al.

(10) Patent No.: US 11,501,852 B2
(45) Date of Patent: Nov. 15, 2022

(54) BLOOD CELL ANALYSIS METHOD AND BLOOD CELL ANALYZER

(71) Applicant: SHENZHEN MINDRAY BIO-MEDICAL ELECTRONICS CO., LTD., Shenzhen (CN)

(72) Inventors: Bo Ye, Shenzhen (CN); Changsong Hu, Shenzhen (CN); Huan Qi, Shenzhen (CN); Wenbo Zheng, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 694 days.

(21) Appl. No.: 16/542,267

(22) Filed: Aug. 15, 2019

(65) Prior Publication Data

US 2019/0371434 A1 Dec. 5, 2019

Related U.S. Application Data

(63) Continuation-in-part of application No. PCT/CN2017/073971, filed on Feb. 17, 2017.

(51) Int. Cl.
*G16B 45/00* (2019.01)
*G01N 1/31* (2006.01)
(Continued)

(52) U.S. Cl.
CPC .............. *G16B 45/00* (2019.02); *G01N 1/14* (2013.01); *G01N 1/31* (2013.01); *G01N 15/1459* (2013.01);
(Continued)

(58) Field of Classification Search
CPC ....... G01N 15/1459; G01N 2015/1006; G01N 2015/008; G01N 33/5094; G01N 21/64; G01N 2015/0084; G01N 2015/1486; G01N 2015/0073; G01N 33/80; G01N 15/14; G01N 2015/149; G01N 2021/4707;
(Continued)

(56) References Cited

U.S. PATENT DOCUMENTS

| 4,637,986 | A | 1/1987 | Brown et al. |
| 6,228,652 | B1* | 5/2001 | Rodriguez ............. G01N 15/14 436/63 |
| 2010/0273168 | A1* | 10/2010 | Krockenberger .. G01N 15/1429 435/6.12 |

FOREIGN PATENT DOCUMENTS

| CN | 101236195 A | 8/2008 |
| CN | 101726579 A | 6/2010 |

(Continued)

*Primary Examiner* — Dean Kwak
(74) *Attorney, Agent, or Firm* — Kory D. Christensen

(57) ABSTRACT

A blood cell analysis method and a blood cell analyzer are provided. In the method and analyzer, characteristic information of white blood cell fragments is obtained based on side scattered light information and fluorescence information, characteristic information of platelets is obtained based on forward scattered light information and fluorescence information and then a count value for the platelets is acquired based on the characteristic information of the platelets and the characteristic information of the white blood cell fragments. The present invention can avoid the influence of the white blood cell fragments on the platelet counting, thereby ensuring the accuracy of the platelet counting without increasing costs.

14 Claims, 6 Drawing Sheets

(51) Int. Cl.
*G01N 15/14* (2006.01)
*G01N 33/50* (2006.01)
*G01N 15/00* (2006.01)
*G01N 1/14* (2006.01)

(52) U.S. Cl.
CPC . *G01N 33/5094* (2013.01); *G01N 2001/1418* (2013.01); *G01N 2015/008* (2013.01); *G01N 2015/0084* (2013.01); *G01N 2015/1486* (2013.01)

(58) Field of Classification Search
CPC ..... G01N 33/56972; G01N 2015/0076; G01N 21/47; G01N 15/12; G01N 2021/4711; G01N 21/6486; G01N 15/06; G01N 15/1434; G01N 15/147; G01N 1/31; G01N 2015/1062; G01N 33/4915; G01N 15/0266; G01N 15/10; G01N 15/1404; G01N 1/14; G01N 2001/1418; G16B 45/00
See application file for complete search history.

(56) References Cited

FOREIGN PATENT DOCUMENTS

| CN | 104749144 A | 7/2015 |
|----|-------------|--------|
| CN | 104965068 A | 10/2015 |
| CN | 106018771 A | 10/2016 |

\* cited by examiner

BLOOD CELL ANALYSIS METHOD AND BLOOD CELL ANALYZER

CROSS-REFERENCE TO RELATED APPLICATIONS

This application is a continuation-in-part of Patent Cooperation Treaty Application No. PCT/CN2017/073971, filed on Feb. 17, 2017, the content thereof is hereby incorporated by reference in its entirety.

TECHNICAL FIELD

The present invention relates to the medical equipment field, and in particular to a blood cell analysis method and a blood cell analyzer.

BACKGROUND

In recent years, blood cell analyzers that count and classify blood cells using flow cytometry have been introduced in succession. Traditional blood cell analyzers use the Coulter principle (also known as the resistance method) for counting platelets, but such analyzers are easily influenced by small red blood cells and red blood cell fragments. In recent years, a method for counting platelets by fluorescent staining and laser scattering, also known as an optical method for counting platelets, has become widely used. This method is based on the following principle: photoelectric signals are generated by laser-irradiating cells that are previously treated with a fluorescent reagent. Different types of cells can be differentiated since different photoelectric signals, e.g. forward scattered light signals and fluorescent signals, can reflect physical and chemical characteristics of cells, e.g. size and granularity of cells and expression of antigen molecules. To a certain extent, the influence of small red blood cells and red blood cell fragments on platelet counting is thereby avoided. However, with further research, it has been found that white blood cell fragments will affect platelet count values and cause inaccuracy in platelet counting.

In the optical method for counting platelets described above, although the influence of white blood cell fragments on the platelet counting can be avoided by establishing a new detecting channel and adding a new reagent, such implements would significantly increase equipment costs and time costs.

SUMMARY

Based on what has been described, it is necessary to provide a blood cell analysis method and a blood cell analyzer to overcome the deficiencies in the prior art mentioned above, which can reduce the interference of possible white blood cell fragments on the platelet counting.

A blood cell analysis method is provided, comprising:
providing a blood sample;
making cells in the blood sample pass through a detection area of a blood cell analyzer one by one to obtain forward scattered light information, side scattered light information, and fluorescence information of each cell;
generating a first scattergram based on the forward scattered light information and the fluorescence information to obtain characteristic information of platelets;
generating a second scattergram based on the side scattered light information and the fluorescence information to obtain characteristic information of white blood cell fragments;
acquiring a count value for the platelets based on the characteristic information of the platelets and the characteristic information of the white blood cell fragments.

A blood cell analyzer is provided, comprising:
a sampling device configured to aspirate a predetermined amount of a blood sample;
a sample preparation device configured to conduct a pretreatment on the blood sample to obtain a pretreated blood sample, wherein the pretreatment comprises fluorescently staining cells in the blood sample and sphering red blood cells in the blood sample;
a detection device configured to make the cells in the pretreated blood sample pass through a detection area one by one and detect forward scattered light information, side scattered light information, and fluorescence information of each cell; and
an analysis device configured to generate a first scattergram based on the forward scattered light information and the fluorescence information detected by the detection device, generate a second scattergram based on the side scattered light information and the fluorescence information, obtain characteristic information of platelets from the first scattergram, obtain characteristic information of white blood cell fragments from the second scattergram, and acquire a count value for the platelet based on the characteristic information of the platelets and the characteristic information of the white blood cell fragments.

In the above method and analyzer, the platelets and the white blood cell fragments are differentiated on a fluorescence-side scattered light scattergram to avoid the influence of the white blood cell fragments on the platelet counting, thereby ensuring the accuracy of the platelet counting without increasing costs.

DETAILED DESCRIPTION

Figure 1:
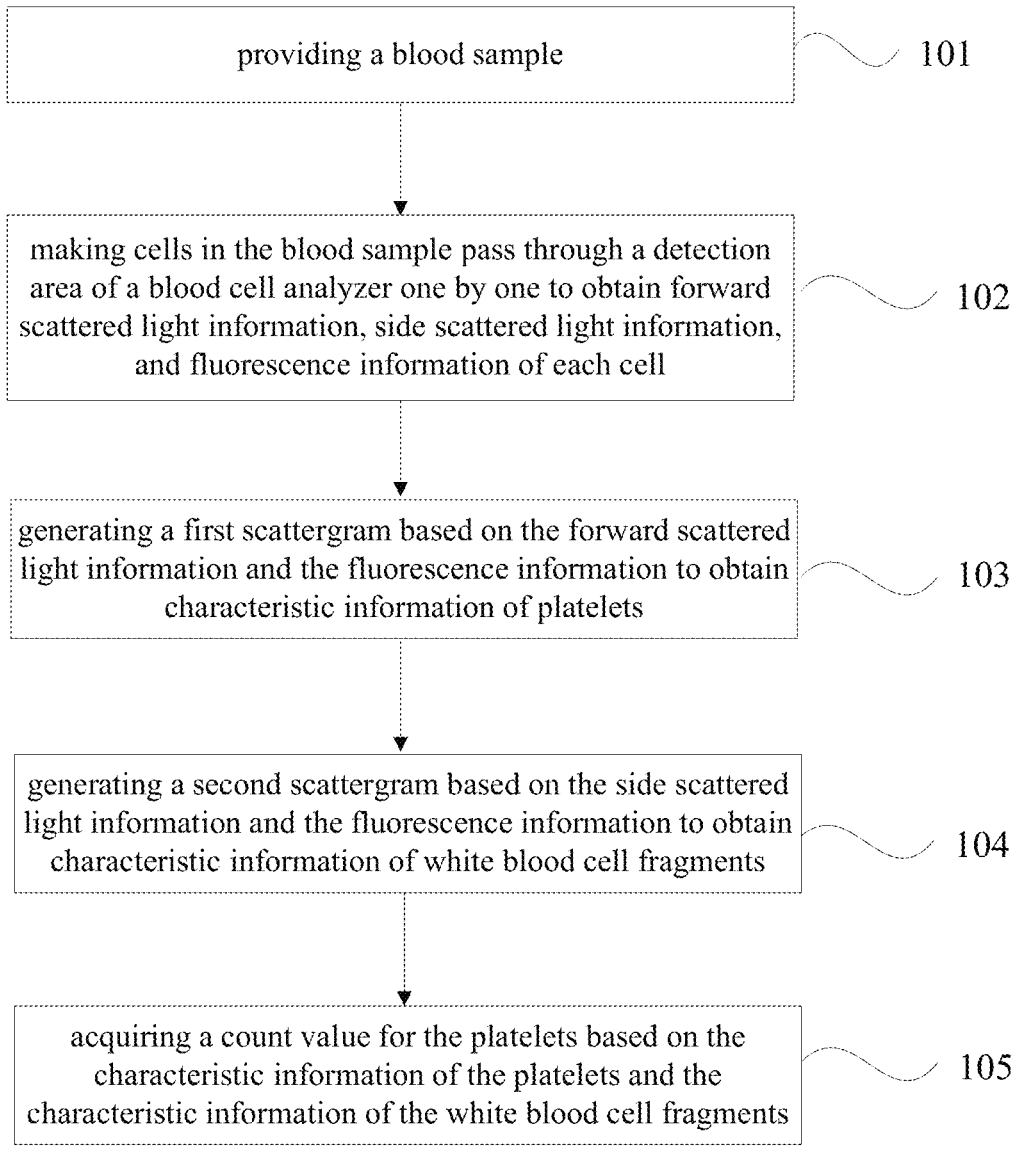
FIG. 1 is a schematic flow chart of a blood cell analysis method according to an embodiment of the present invention.

White blood cell fragments, also known as fragmented white blood cells, are white blood cells with cell membranes that are broken completely or partially. Particles and nuclear contents released upon fragmentation of white blood cells are scattered and vary in size. Small white blood cell fragments have a similar size with platelets.

Scattergrams can be obtained by detecting, one by one with flow cytometry, forward scattered light information, side scattered light information, and fluorescence information of cells in blood samples treated with reagents. A scattergram is a two-dimensional diagram generated by a cell analyzer using flow cytometry, with two-dimensional characteristic information of particles distributed thereon. The X-coordinate axis and the Y-coordinate axis of the scattergram respectively characterize a characteristic of each particle. For example, on a scattergram, the Y-coordinate axis characterizes forward scattered light intensity, and the X-coordinate axis characterizes fluorescence intensity. Using forward scattered light-fluorescence scattergrams, blood cells can be classifies into at least three categories: white blood cells, red blood cells, and platelets.

Analysis of blood samples containing white blood cell fragments and normal blood samples (substantially free of white blood cell fragments) was carried out through indepth research. It was unexpectedly found that a particle population appearing in a specific region on the two-dimensional scattergram obtained by fluorescence information and side scattered light information, have a strong correlation with the existence of white blood cell fragments.

While not wishing to be bound by theory, the inventors speculate that cell membranes of white cell fragments are completely or partially broken, and particles and nuclear contents released upon fragmentation of white blood cells are scattered and vary in size. Small white blood cell fragments have a similar size with platelets. In the optical method for counting platelets, since the forward scattered light characterizes the size of particles, it is difficult to distinguish between forward scattered light information generated by white blood cell fragments with a small size and forward scattered light information generated by platelets. Since the white blood cell fragments contain nucleic acid substances, relatively strong fluorescence would be generated by the white blood cell fragments. When using the optical method for counting platelets, since the fluorescence information characterizes the nucleic acid content of particles, fluorescence information intensity generated by the white blood cell fragments is close to that of the platelets, in particular large platelets, and fluorescence information generated by the white blood cell fragments is difficult to distinguish from that of the platelets. When using the optical method for counting platelets, platelets are determined from forward scattered light and fluorescence. Therefore, on the forward scattered light-fluorescence scattergram, the counting of platelets is affected by white blood cell fragments, resulting in inaccurate counting. It is found through research and analysis that, since white blood cell fragments are fragmented cells, the intensity of side scattered light information that characterizes cell contents is weakened, and platelets and white blood cell fragments can be better differentiated on a fluorescence-side scattered light scattergram. Therefore, the present invention uses the above findings to perform classification and accurate counting of blood cells.

As shown in FIG. 1, a blood cell analysis method is provided according to an embodiment of the present invention, comprising the following steps:

Step 101, providing a blood sample. Specifically, the blood sample needs to be subjected to a specific treatment. For example, red blood cells in the blood sample is sphered or the blood sample is proportionally mixed with a fluorescent dye reagent. The aforementioned sphering treatment of the red blood cells in the blood sample means keeping cell membranes of the red blood cells substantially intact without lysing the red blood cells.

Step 102, making cells in the blood sample pass through a detection area of a blood cell analyzer one by one, to obtain forward scattered light information, side scattered light information, and fluorescence information of each cell. Because red blood cells, white blood cells, and platelets in the blood sample have different abilities to bind to a fluorescent dye, they would generate different fluorescence information. In addition, since the above various types of cells have different sizes, they would generate different forward scattered light information, and because of the difference in intracellular morphology or complexity of the cells, they would generate different side scattered light information. Therefore, by making the cells pass through the detection area one by one and collecting those information, it is possible to differentiate the above types of cells on a scattergram.

Step 103, generating a first scattergram based on the forward scattered light information and the fluorescence information to obtain characteristic information of platelets, namely information that characterizing the platelets. In an embodiment, the blood cells can be classified into at least three types of white blood cells, red blood cells, and platelets, based on the first scattergram generated from the forward scattered light information and the fluorescence information, i.e. a forward scattered light-fluorescence scattergram. A platelet characterizing count value is acquired by directly collecting statistics on the characteristic information of the platelets, which platelet characterizing count value is not necessarily an accurate platelet count, because the platelet characterizing count value may include a count of white blood cell fragments. In some embodiments, a count value for reticulocytes may also be acquired on the first scattergram.

Step 104, generating a second scattergram based on the side scattered light information and the fluorescence information to obtain characteristic information of white blood cell fragments, namely information that characterizing the white blood cell fragments. It has been found that a particle population appearing in a specific region on the two-dimensional scattergram obtained from the fluorescence information and the side scattered light information has a strong correlation with the existence of white blood cell fragments. Thus, by using the second scattergram to determine the specific region on the second scattergram, the characteristic information of white blood cell fragments may be obtained, thereby differentiating the white blood cell fragments from the platelets to acquire a count for the white blood cell fragments.

Step 105, acquiring a real count value for the platelets based on the characteristic information of the platelets and the characteristic information of the white blood cell fragments obtained in the above two steps, by means of a specific algorithm or processing.

For example, a platelet characterizing count value may be acquired based on the characteristic information of the platelets obtained from the first scattergram, a white blood cell fragment characterizing count value may be acquired based on the characteristic information of the white blood cell fragments obtained from the second scattergram, and the count value for the platelets may be acquired by subtracting the white blood cell fragment characterizing count value from the platelet characterizing count value.

In another example, scattered points representing the characteristic information of the white blood cell fragments on the first scattergram are determined based on the characteristic information of the white blood cell fragments obtained in Step 104. These scattered points representing the white blood cell fragments are removed from the first scattergram, so that the characteristic information of the white blood cell fragments is erased from the characteristic information of the platelets on the first scattergram, so as to obtain accurate platelet information, and so the count value for the platelets can be acquired from the platelet information.

In some embodiments, the blood cell analysis method further comprises: acquiring a count value for the white blood cell fragments based on the characteristic information of the white blood cell fragments; determining whether the count value for the white blood cell fragments exceeds a threshold value; and prompting that white blood cell fragments exist in the blood sample, if the count value for the white blood cell fragments exceeds the threshold value. The prompting may be implemented in a form of text, sound, light, or pop-up window.

In some embodiments, the blood cell analysis method further comprises providing a display device for displaying the obtained scattergrams. More specifically, on the display device, based on the characteristic information of the white blood cell fragments obtained in Step 104, the platelets and the white blood cell fragments can be visually distinguished on the first scattergram, for example, displayed as scattered points in different colors/shapes or displayed by drawing respective boundaries or contours, so that the platelets and the white blood cell fragments can be visually distinguished on the first scattergram.

In order to facilitate a further understanding of the present invention, two embodiments are described below in combination with the accompanying drawings.

Embodiment 1

Figure 2:
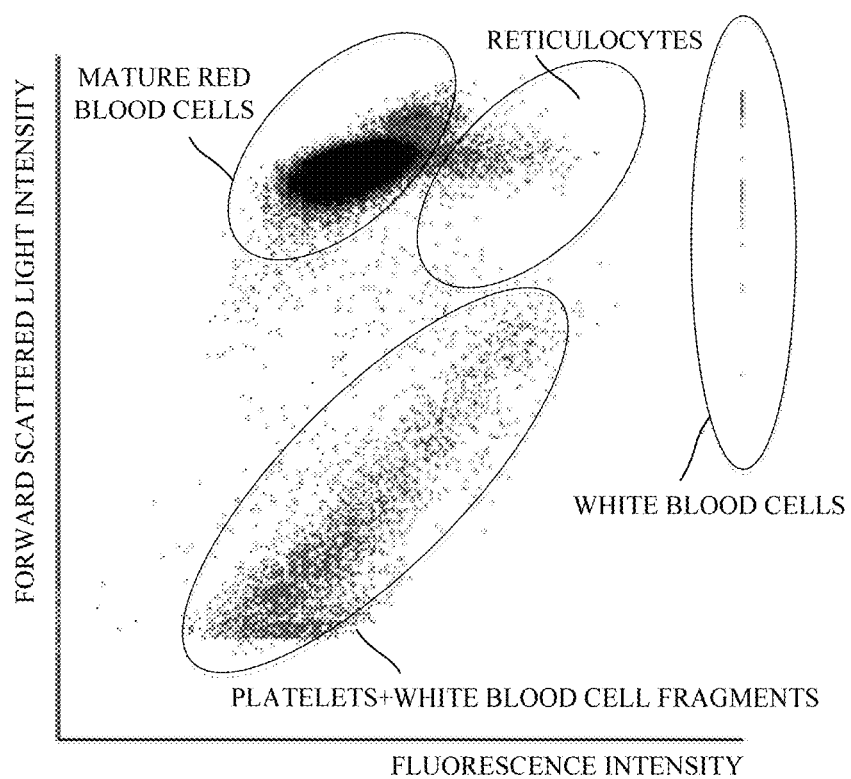
FIG. 2 is a forward scattered light-fluorescence scattergram of a first blood sample containing white blood cell fragments.
Figure 3:
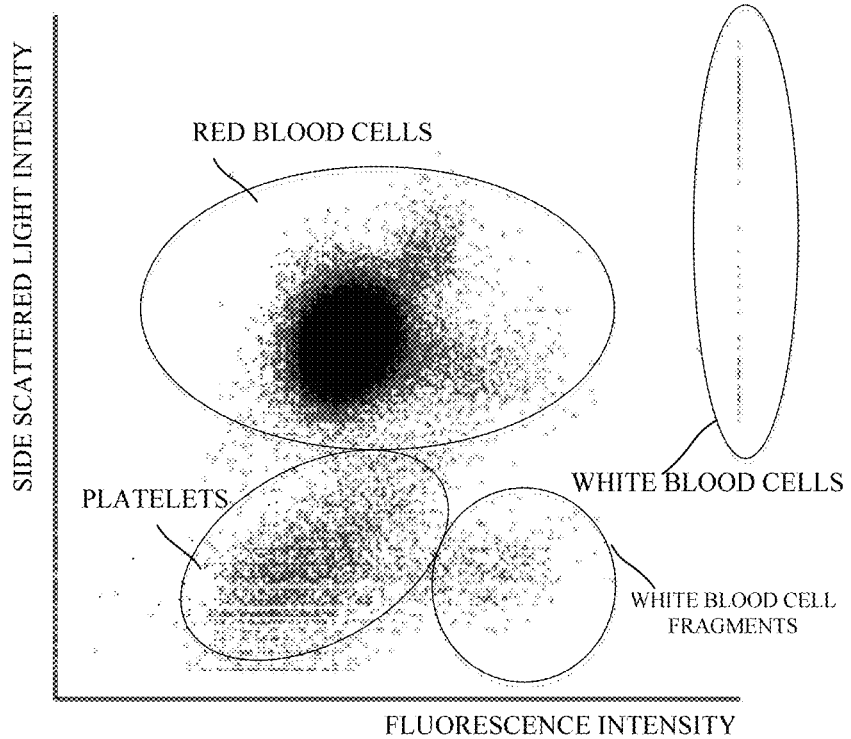
FIG. 3 is a side scattered light-fluorescence scattergram of the first blood sample.

A first blood sample containing white blood cell fragments was provided. The first blood sample was treated so that red blood cells were sphered and remain substantially intact. Cells were made pass through a detection area of a blood cell analyzer one by one, and three signals of each cell, namely forward scattered light, side scattered light and fluorescence, were detected. FIG. 2 shows a forward scattered light-fluorescence scattergram of the first blood sample (a first scattergram), and FIG. 3 shows a side scattered light-fluorescence scattergram of the first blood sample (a second scattergram). In FIG. 2, the platelets and the white blood cell fragments are not well differentiated, and therefore an accurate platelet count value cannot be acquired. In FIG. 3, the platelets and the white blood cell fragments are well differentiated, but the platelets and the red blood cells are not well differentiated. Therefore, a number of the white blood cell fragments can be calculated by using FIG. 3 and then fed back to FIG. 2. In this way, not only a count value for the platelets can be acquired, but also count values of other types of cells, such as the red blood cells, can be acquired at the same time. Specifically, scattered points in a predetermined characteristic region, where the white blood cell fragments are located in FIG. 3, correspond to respective scattered points in FIG. 2 and are marked with a different color in FIG. 2. Alternatively, a scattered point count of the white blood cell fragments located in the predetermined characteristic region in FIG. 3 is directly subtracted from a scattered point count of the platelets and white blood cell fragments in FIG. 2, so as to acquire the platelet count value. On the second scattergram, a region, in which cells having side scattered light intensity smaller than that of the red blood cells and fluorescence intensity larger than that of the platelets are located, is determined as the predetermined characteristic region, and scattered points falling within the predetermined characteristic region are identified as the white blood cell fragments.

The position and size of this predetermined characteristic region may be fixed (i.e. predetermined) or may be dynamically changed with the positions of the platelets and the white blood cell fragments on the side scattered light-fluorescence scattergram in accordance with a specific rule. For example, the lower boundary of the red blood cells, the right boundary of the platelets, and the left boundary of the white blood cells can be determined. The lower boundary of the red blood cells, the right boundary of the platelets, the left boundary of the white blood cells and the horizontal axis are respectively used as the upper boundary, the left boundary, the right boundary, and the lower boundary of the predetermined characteristic region. The lower boundary of the red blood cells may also be moved downward by a specific distance and then used as the upper boundary of the predetermined characteristic region, or the right boundary of the platelets may be moved to the right by a specific distance and then used as the left boundary of the predetermined characteristic region.

The position and size of the predetermined characteristic region may also be determined as follows. A normal blood sample containing no white blood cell fragments and an abnormal blood sample known to contain white blood cell fragments are measured in a same detecting system, and side scattered light-fluorescence scattergrams of both the samples are then obtained. By comparing the two side scattered light-fluorescence scattergrams, a region, in which on the side scattered light-fluorescence scattergram of the normal blood sample exists a particle population (for example, as shown in FIG. 3) and in which on the side scattered light-fluorescence scattergram of the abnormal blood sample exist no particle population (for example, as shown in FIG. 4), will be found on the right side of a region where platelets are located and can be determined as the predetermined characteristic region.

Figure 4:
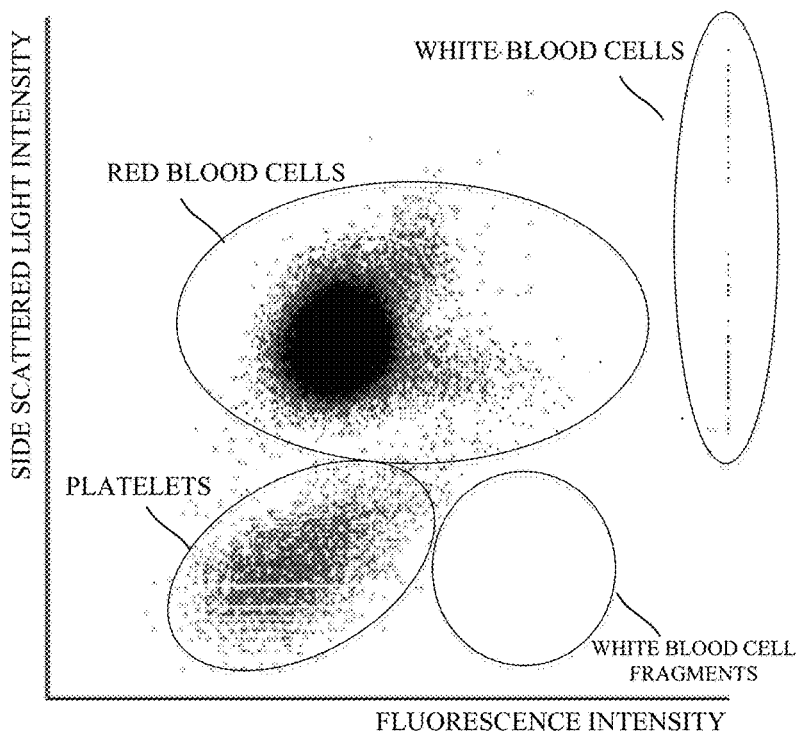
FIG. 4 is a side scattered light-fluorescence scattergram of a normal blood sample without white blood cell fragments.

As can be seen from FIG. 4, on the forward scattered light-fluorescence scattergram of the normal blood sample, red blood cells, white blood cells, and platelets are respectively distributed in a specific region of the scattergram, and these regions are clearly separated. Therefore, the forward scattered light-fluorescence scattergram can be used to count the red blood cells, the white blood cells, and the platelets more accurately.

Embodiment 2

Figure 5:
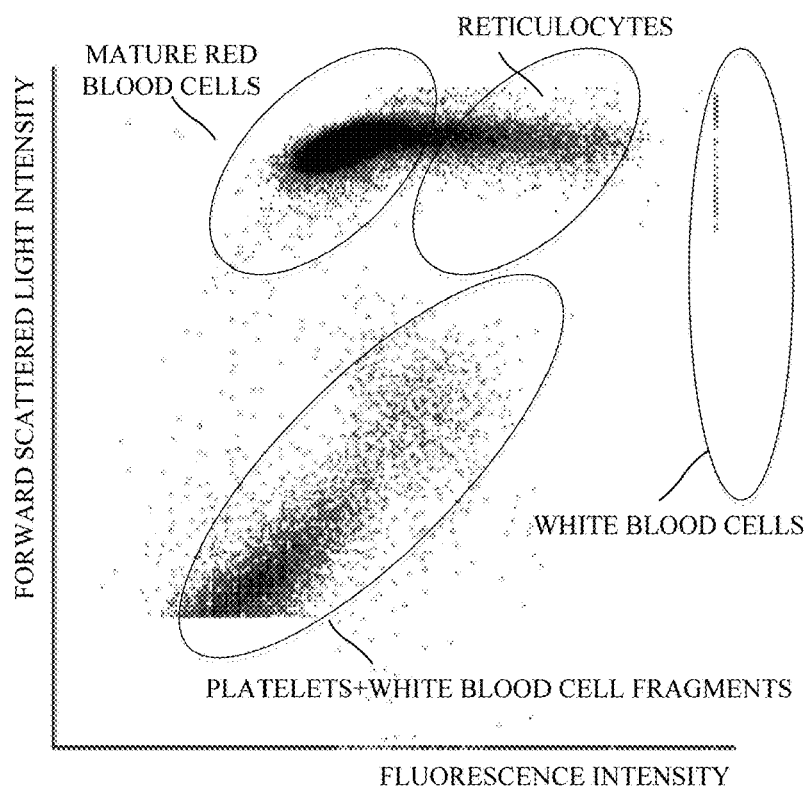
FIG. 5 is a forward scattered light-fluorescence scattergram of a second blood sample containing white blood cell fragments.
Figure 6:
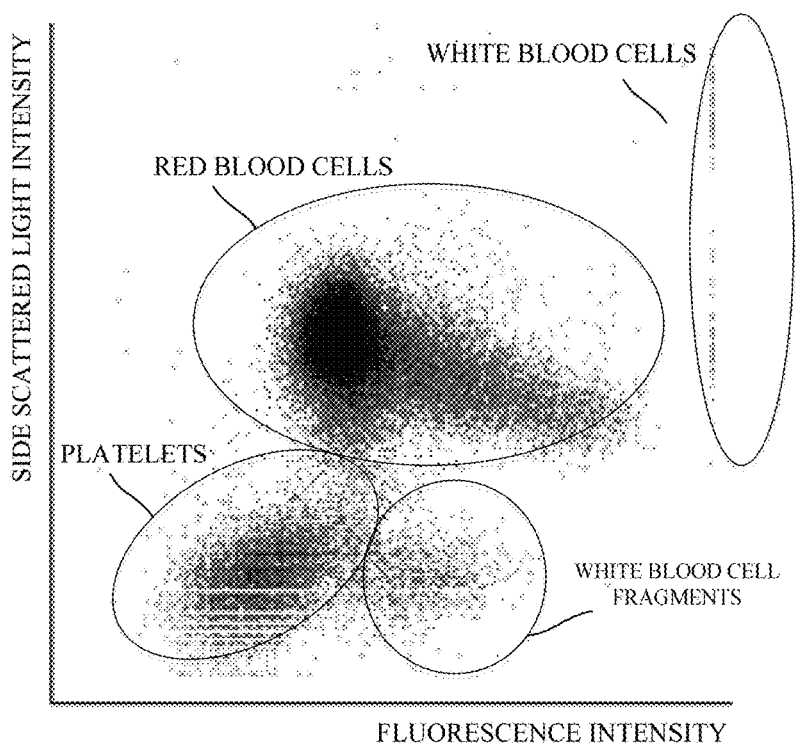
FIG. 6 is a side scattered light-fluorescence scattergram of the second blood sample containing white blood cell fragments.
Figure 7:
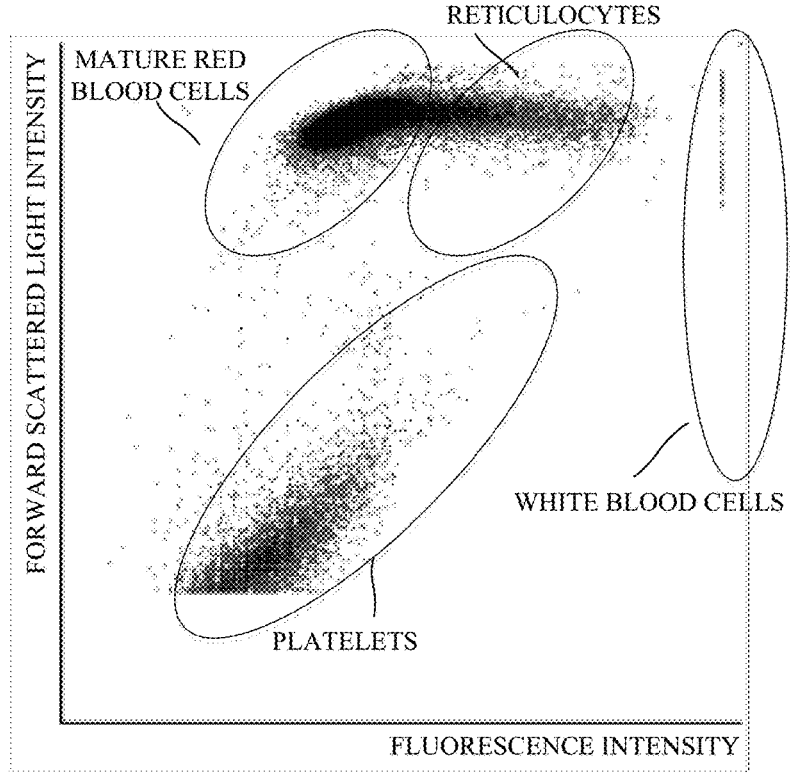
FIG. 7 is a forward scattered light-fluorescence scattergram obtained after removing white blood cell fragment scattered points from the second blood sample.

A second blood sample containing white blood cell fragments was provided. The second blood sample was treated so that red blood cells were sphered and remain substantially intact. The cells were made pass through a detection area of a blood cell analyzer one by one, and three signals of each cell, namely forward scattered light, side scattered light and fluorescence, were detected. FIG. 5 shows a forward scattered light-fluorescence scattergram of the second blood sample, and FIG. 6 shows a side scattered light-fluorescence scattergram of the second blood sample. In FIG. 5, the platelets and the white blood cell fragments are not well differentiated, and therefore an accurate platelet count value cannot be acquired. In FIG. 6, the platelets and the white blood cell fragments are well differentiated, but the platelets and the red blood cells are not well differentiated. Therefore, a predetermined characteristic region can be determined in FIG. 6, and scattered points representing white blood cell fragment information can be identified in this predetermined characteristic region to acquire a count value for the white blood cell fragments. Then, in FIG. 5, scattered points corresponding to these white blood cell fragments are removed to obtain a forward scattered light-fluorescence scattergram with the white blood cell fragment scattered points removed as shown in FIG. 7. Mature red blood cells, reticulocytes, white blood cells, and platelets can be identified and counted in FIG. 7.

The risk of having white blood cell fragments mistakenly counted into the number of platelets can be avoided, thereby more accurately reflecting the composition of various blood cells.

In the above method, since it is not necessary to establish a new channel or use an additional reagent, it is possible to differentiate between white blood cell fragments and platelets and count the number of cells, such as platelets, with effectively controlled costs. Existing blood cell analyzers have a reticulocyte detecting channel for using forward scattered light and fluorescence to classify and count reticulocytes and other cells in a blood sample, and also capable of classifying and counting platelets and other cells. However, as explained above, platelet classification and counting may be interferred with white blood cell fragments in the blood sample, thus affecting the accuracy of measurement results. With the method of the present invention, it is possible to accurately report the reticulocyte count and the platelet count in the reticulocyte detecting channel without substantially increasing costs.

In the above method, the characteristic cells falling within the predetermined characteristic region may also be marked, removed, or reported by an alarm prompt. By means of marking, the marked characteristic cells may also be observed on other two-dimensional or three-dimensional diagrams generated based on the detected forward scattered light information, side scattered light information, and fluorescence information. Similarly, the reported alarm prompt can appear on the other two-dimensional or three-dimensional diagrams. In case of removing the characterized cells, the influence of the white blood cell fragments on the accuracy of the platelet number is avoided, and various types of two-dimensional or three-dimensional diagrams are generated using the detected forward scattered light information, side scattered light information, and fluorescence information, so that various types of cells can be accurately differentiated on the scattergrams.

The analysis method provided by the present invention will be further illustrated by a comparative embodiment as follows.

A blood sample containing white blood cell fragments was tested by a BC-6800 blood cell analyzer manufactured by Shenzhen Mindray Bio-Medical Electronics Co., Ltd. and a BriCyte E6 blood cell analyzer manufactured by Shenzhen Mindray Bio-Medical Electronics Co., Ltd (the latter is expensive, but is capable of differentiating between white blood cell fragments and platelets. A test result, which is obtained by using the flow cytometry RBC/PLT ratio method recommended by the International Council for Standardization in Haematology (ICSH), is used as a reference value). The results are as follows:

By using the BC-6800 blood cell analyzer, a platelet value was 179 ($10^9$/L) when the above method was not used, and a platelet value was 144 ($10^9$/L) when the above method was used to avoid the influence of white blood cell fragments.

A platelet value obtained by the BriCyte E6 flow cytometer was 141 ($10^9$/L).

It can be seen that, when the blood sample containing white blood cell fragments was tested using the above method, the platelet value was closer to the reference value, and thus a more accurate platelet count can be obtained by using the above method with a relatively low cost device.

Figure 8:
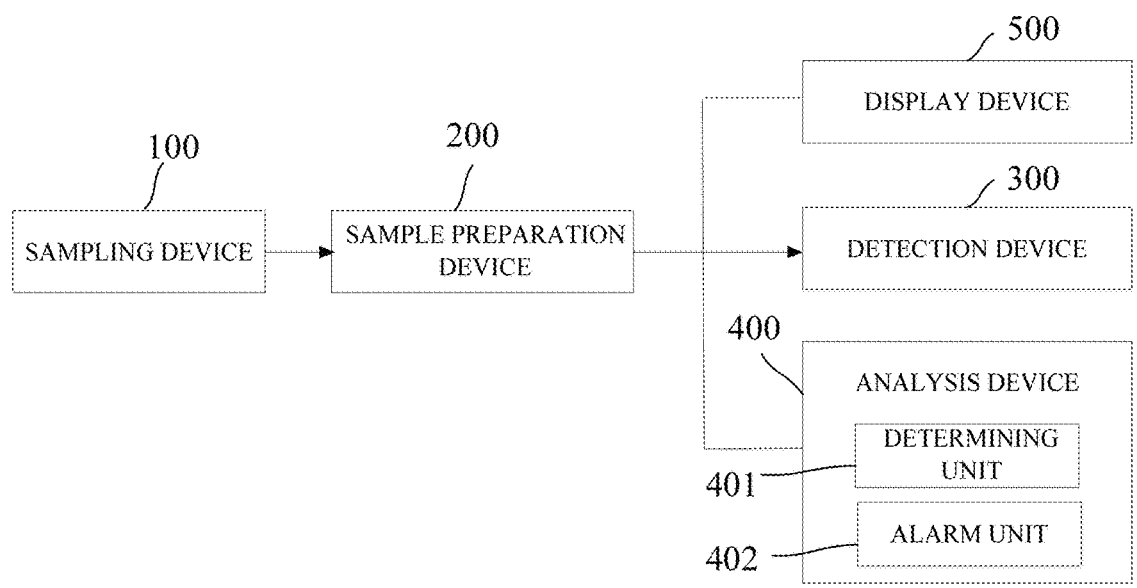
FIG. 8 is a structural block diagram of a blood cell analyzer according to an embodiment of the present invention.

Referring to FIG. 8, accordingly, the present invention also provides a blood cell analyzer comprising a sampling device 100, a sample preparation device 200, a detection device 300, and an analysis device 400.

The sampling device 100 is configured to aspirate a predetermined amount of a blood sample.

The sample preparation device 200 is configured to conduct a pretreatment on the blood sample to obtain a pretreated blood sample, the pretreatment comprising staining cells in the blood sample with a fluorescent dye and sphering red blood cells in the blood sample. After the red blood cells are sphered, membranes of the red blood cells can remain substantially intact.

Figure 9:
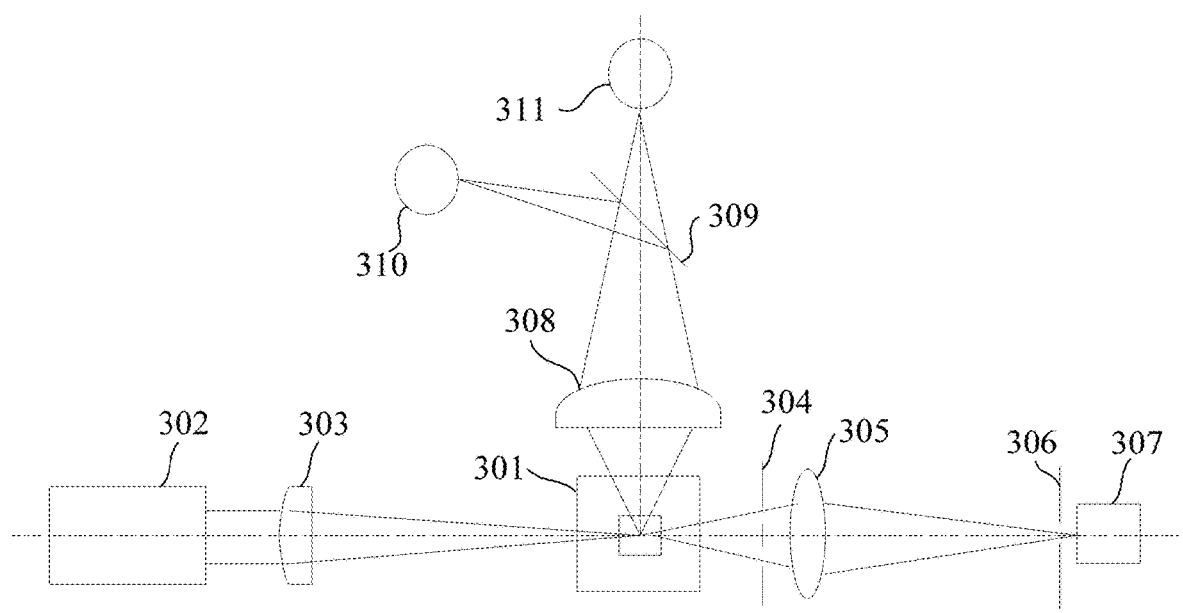
FIG. 9 is a structural schematic diagram of a detection area of a blood cell analyzer according to an embodiment of the present invention.

The detection device 300 is configured to make the cells in the pretreated blood sample pass through a detection area one by one and detect forward scattered light information, side scattered light information, and fluorescence information of each cell in the blood sample. Referring also to FIG. 9, in particular, the detection device 300 is provided with a flow chamber 301, through which the cells pass one by one. A laser 302 emits laser light. Then, the laser light is focused by a focusing lens 303 and aligned with the flow chamber 301. When the cells flow through the flow chamber 301, photoelectric signals are generated by the cells upon laser irradiation, wherein a forward scattered light signal is generated along a laser irradiation direction, and a side scattered light signal and a fluorescent signal are generated offset (generally 90 degrees) from the laser irradiation direction. In the laser irradiation direction, a diaphragm 304, a collecting lens 305, a flare eliminating diaphragm 306, and a forward scattered light detector 307 are sequentially arranged, and the forward scattered light signal is collected by the forward scattered light detector 307. In a direction offset from the laser irradiation direction, another collecting lens 308 and a dichroic mirror 309 are sequentially arranged. The side scattered light signal and the fluorescent signal are separated by the dichroic mirror 309 and are respectively collected by a side scattered light detector 310 and a fluorescence detector 311. The above detection is performed in the same channel, and the forward scattered light information, the side scattered light information, and the fluorescence information of the cells in the blood sample are collected without establishing a new channel and using additional pretreatment reagents.

The analysis device 400 is configured to generate a first scattergram based on the forward scattered light information and the fluorescence information detected by the detection device 300, generate a second scattergram based on the side scattered light information and the fluorescence information, obtain characteristic information of platelets from the first scattergram, obtain characteristic information of white blood cell fragments from the second scattergram, and acquire a count value for the platelets based on the characteristic information of the platelets and the characteristic information of the white blood cell fragments.

The analysis device 400 may be implemented a processor. The processor may be a microprocessor, microcontroller, digital signal processor, dedicated or general purpose programmed chip.

Furthermore, the analysis device 400 comprises a determining unit 401 and an alarm unit 402. The determining unit 401 is configured to acquire a count value for the white blood cell fragments based on the characteristic information of the white blood cell fragments and to determine whether the count value for the white blood cell fragments exceeds a threshold value. The alarm unit 402 is configured to determine whether to output an alarm prompt based on the determination result of the determining unit 401. For example, when the determining unit 401 determines that the count value for the white blood cell fragments exceeds the threshold value, the alarm unit 402 will output an alarm prompt.

Further, the blood cell analyzer further comprises a display device 500, which is configured to display the obtained scattergrams, for example, the first scattergram and the second scattergram described above, or other two-dimensional or three-dimensional scattergrams. The display device 500 can display the platelets and the white blood cell fragments in a visual and distinguishable way on the first scattergram based on the characteristic information of the white blood cell fragments, for example, by displaying them as scattered points in different colors/shapes, or by drawing respective boundaries or contours thereof.

Figure 10:
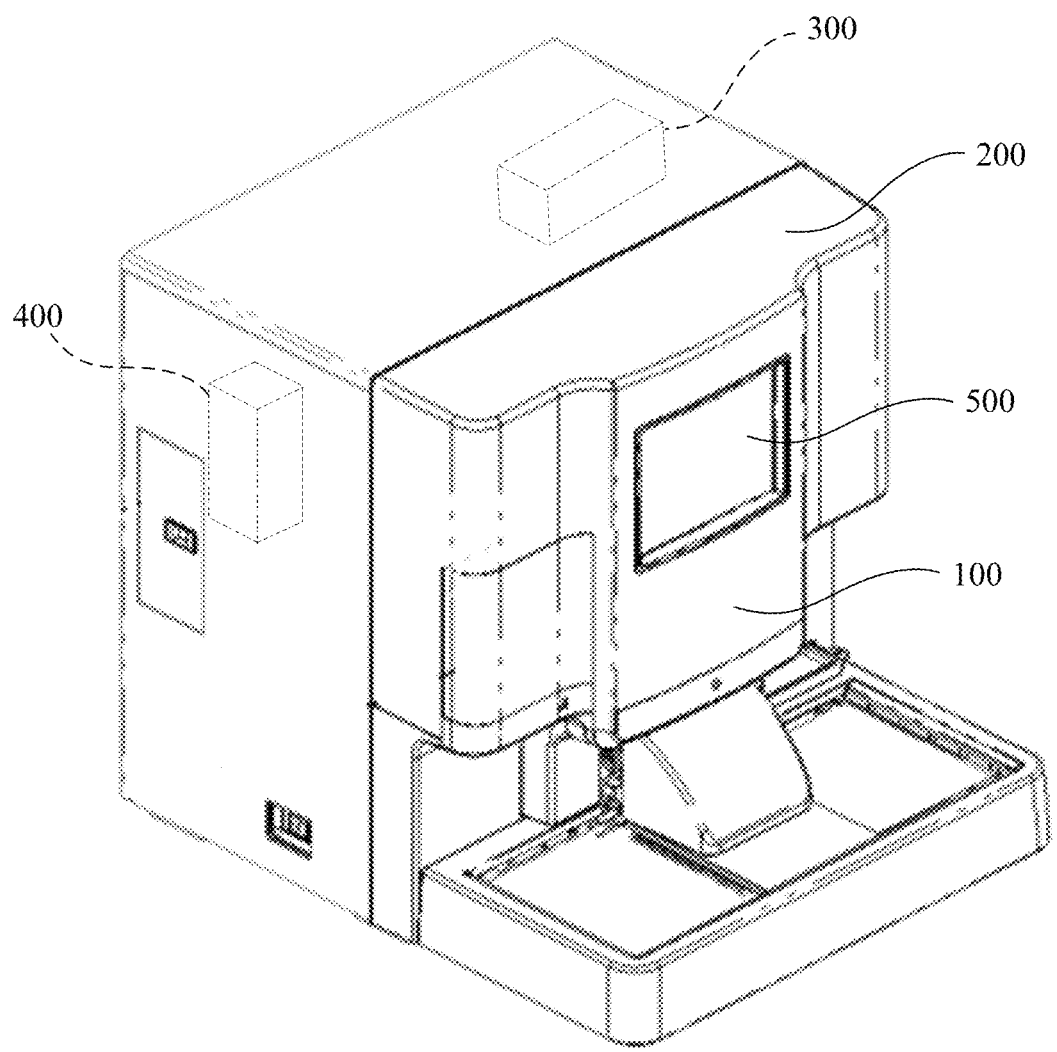
FIG. 10 is a schematic view of an outer configuration of a blood cell analyzer according to an embodiment of the present invention.

FIG. 10 is a schematic view of an outer configuration of a blood cell analyzer according to an embodiment. The blood cell analyzer has a housing with a substantially cubic structure. The sampling device 100 is exposed outside the housing to facilitate the aspiration of a blood sample. More specifically, the housing may also be provided with a sample placement stage, and the sampling device 100 may aspirate a blood sample placed on the sample placement stage. The sample preparation device 200, the detection device 300, and the analysis device 400 are all accommodated in the housing. The display device 500 is located on the surface of the housing for displaying information such as detection results of the blood cell analyzer. The above blood cell analyzer has a neat appearance and is convenient for operation.

It will be understood that, a person skilled in the art can appreciate that the modules and method steps described in combination with the examples disclosed herein can be implemented using electronic hardware, computer software, or any combination thereof. Whether such functionality is implemented as hardware or software depends upon the particular application of the technical solution and design constraints. A person skilled in the art may implement the described functionality in varying ways for each particular application, but such implementations should not be interpreted as causing a departure from the scope of the present application.

In the embodiments of the present application, the disclosed device and method may be implemented in other manners. For example, the embodiments of the foregoing device are merely illustrative. For example, the division of units is only a division of logical functions, and in actual implementations, there may be other division methods in actual implementations. For example, multiple units may be combined or may be integrated in one system.

When being implemented as a software function unit and sold or used as a stand-alone product, the functionality of the unit may be stored in a computer-readable storage medium. Based on such understanding, the technical solution of the present application substantially, or the part thereof that contributes to the prior art, may be embodied in a software product. The computer software product is stored in a storage medium and includes instructions for causing a computer device to execute all or part of the steps of the methods described in any embodiments of the present application.

The foregoing storage medium may be any medium that can store program code, such as a USB flash disk, a mobile hard disk, a read only memory, or a random access memory.

The technical features of the above-described embodiments may be combined in any combination. For the sake of brevity of description, the various technologies in the above embodiments are not described in all possible combinations. However, as long as no contradiction occurs in a combination of these technical features, the combination should be considered to fall within the scope of the present specification.

The above-described embodiments are merely illustrative of several embodiments of the present application, and the description thereof is specific and detailed, but it is not to be construed as limiting the scope of the application. It should be noted that for a person of ordinary skill in the art, several variations and improvements can be made without departing from the spirit of the present application, which shall fall within the scope of the application. Accordingly, the protection scope of the present patent shall be subject to the appended claims.

The invention claimed is:

1. A blood cell analysis method, comprising:
   providing a blood sample;
   making cells in the blood sample pass through a detection area of a blood cell analyzer one by one to obtain forward scattered light information, side scattered light information, and fluorescence information of each cell;
   generating a first scattergram based on the forward scattered light information and the fluorescence information to obtain characteristic information of platelets;
   generating a second scattergram based on the side scattered light information and the fluorescence information to obtain characteristic information of white blood cell fragments; and
   acquiring a count value for the platelets based on the characteristic information of the platelets and the characteristic information of the white blood cell fragments.

2. The blood cell analysis method according to claim 1, further comprising:
   acquiring a count value for the white blood cell fragments based on the characteristic information of the white blood cell fragments;
   determining whether the count value for the white blood cell fragments exceeds a threshold value; and
   prompting that white blood cell fragments exist in the blood sample, if the count value for the white blood cell fragments exceeds the threshold value.

3. The blood cell analysis method according to claim 2, wherein the prompting is implemented in a form of text, sound, light, or pop-up window.

4. The blood cell analysis method according to claim 1, wherein the step of acquiring a count value for the platelets based on the characteristic information of the platelets and the characteristic information of the white blood cell fragments, comprises:
   acquiring a platelet characterizing count value based on the characteristic information of the platelets obtained from the first scattergram;

acquiring a white blood cell fragment characterizing count value based on the characteristic information of the white blood cell fragments obtained from the second scattergram; and acquiring the count value for the platelets by subtracting the white blood cell fragment characterizing count value from the platelet characterizing count value.

5. The blood cell analysis method according to claim 1, wherein the step of acquiring a count value for the platelets based on the characteristic information of the platelets and the characteristic information of the white blood cell fragments, comprises:

removing scattered points characterizing the white blood cell fragments from the first scattergram based on the characteristic information of the white blood cell fragments to obtain platelet information;

acquiring the count value for the platelets based on the platelet information.

6. The blood cell analysis method according to claim 1, further comprising:

providing a display device, displaying the first scattergram on the display device, and displaying the platelets and the white blood cell fragments in a visual and distinguishable way on the first scattergram based on the characteristic information of white blood cell fragments.

7. The blood cell analysis method according to claim 6, wherein the step of displaying the platelets and the white blood cell fragments on the first scattergram, comprises:

displaying the platelets and the white blood cell fragments as scattered points in different colors/shapes or displaying the platelets and the white blood cell fragments by drawing boundaries or contours thereof.

8. The blood cell analysis method according to claim 1, further comprising:

acquiring a count value for reticulocytes and/or a count value for red blood cells based on the first scattergram.

9. The blood cell analysis method according to claim 1, further comprising:

treating the blood sample before making the cells in the blood sample pass one by one through the detection area of the blood cell analyzer, wherein the treating comprises sphering red blood cells and keeping membranes of the red blood cell substantially intact.

10. The blood cell analysis method according to claim 1, wherein cells located in a predetermined characteristic region on the second scattergram are identified as the white blood cell fragments, wherein the cells located in the predetermined characteristic region have side scattered light intensity smaller than that of red blood cells in the blood sample and have fluorescence intensity larger than that of the platelets.

11. The blood cell analysis method according to claim 10, wherein a position and a size of the predetermined characteristic region are fixed.

12. The blood cell analysis method according to claim 10, wherein a position and a size of the predetermined characteristic region are dynamically changed with the positions of the platelets and the white blood cell fragments on the second scattergram.

13. The blood cell analysis method according to claim 12, wherein boundaries of the predetermined characteristic region are determined by a lower boundary of the red blood cells, a right boundary of the platelets, a left boundary of white blood cells in the blood sample.

14. The blood cell analysis method according to claim 10, wherein the predetermined characteristic region is located at a right side of the platelets and at a lower side of the red blood cells on the second scattergram.

* * * * *